United States Patent
Roessl et al.

(10) Patent No.: US 9,177,397 B2
(45) Date of Patent: Nov. 3, 2015

(54) IMAGING APPARATUS

(75) Inventors: Ewald Roessl, Ellerau (DE); Axel Thran, Hamburg (DE); Roland Proksa, Neu Wulmstorf (DE)

(73) Assignee: Koninklijke Philips N.V., Eindhoven (NL)

( * ) Notice: Subject to any disclaimer, the term of this patent is extended or adjusted under 35 U.S.C. 154(b) by 102 days.

(21) Appl. No.: 14/125,149

(22) PCT Filed: Jun. 7, 2012

(86) PCT No.: PCT/IB2012/052865
§ 371 (c)(1),
(2), (4) Date: Dec. 10, 2013

(87) PCT Pub. No.: WO2012/176088
PCT Pub. Date: Dec. 27, 2012

(65) Prior Publication Data
US 2014/0112565 A1  Apr. 24, 2014

(30) Foreign Application Priority Data
Jun. 21, 2011 (EP) .................................. 11305778

(51) Int. Cl.
*G06K 9/00* (2006.01)
*G06T 11/00* (2006.01)
*G01N 23/04* (2006.01)
(Continued)

(52) U.S. Cl.
CPC ............ *G06T 11/005* (2013.01); *G01N 23/046* (2013.01); *A61B 6/032* (2013.01); *A61B 6/482* (2013.01); *A61B 6/583* (2013.01); *G01N 2223/401* (2013.01); *G01N 2223/419* (2013.01); *G06T 2211/408* (2013.01)

(58) Field of Classification Search
USPC .................................................. 382/128–134
See application file for complete search history.

(56) References Cited

U.S. PATENT DOCUMENTS 4,149,248 A * 4/1979 Pavkovich ...................... 378/14
4,217,641 A * 8/1980 Naparstek ..................... 382/131
(Continued)

FOREIGN PATENT DOCUMENTS

WO 2008046498 A1 4/2008

OTHER PUBLICATIONS

Carmi, R., et al.; Material separation with dual-layer CT; 2005; IEEE Conf. record on Nuclear Science Symposium; vol. 4; 1876-1878.
(Continued)

*Primary Examiner* — Alex Liew

(57) ABSTRACT

The invention relates to an imaging apparatus (31) for imaging an object. A reconstruction unit (12) determines component projection data values, which correspond to, for example, a base material of the object, and reconstructs an image of the object based on the determined component projection data values. A component projection data value, which corresponds to a ray, is determined as a combination of weighted base functions, which depend on energy projection data values of the same ray and the orientation of the same ray. This allows considering a possible dependency of the corresponding decomposition on the orientation of the ray, thereby allowing the imaging apparatus to improve the quality of decomposing the provided energy projection data values into the component projection data values and thus of a finally reconstructed image of the object, which is reconstructed based on the component projection data values.

13 Claims, 4 Drawing Sheets

(51) Int. Cl.
*A61B 6/03* (2006.01)
*A61B 6/00* (2006.01)

(56) References Cited

U.S. PATENT DOCUMENTS

| | | | | |
|---|---|---|---|---|
| 4,219,876 | A * | 8/1980 | Mizutani et al. | 378/15 |
| 4,282,438 | A * | 8/1981 | Nishida et al. | 378/11 |
| 4,365,339 | A * | 12/1982 | Pavkovich et al. | 378/15 |
| 4,506,327 | A * | 3/1985 | Tam | 378/5 |
| 4,580,219 | A * | 4/1986 | Pelc et al. | 382/131 |
| 5,165,100 | A * | 11/1992 | Hsieh et al. | 382/131 |
| 5,430,783 | A * | 7/1995 | Hu et al. | 378/15 |
| 5,434,416 | A * | 7/1995 | Motomura et al. | 250/369 |
| 6,631,285 | B2 * | 10/2003 | Natterer et al. | 600/436 |
| 7,197,172 | B1 | 3/2007 | Naidu et al. | |
| 7,734,076 | B2 | 6/2010 | Du et al. | |
| 7,801,264 | B2 | 9/2010 | Wu et al. | |
| 2003/0095695 | A1 * | 5/2003 | Arnold | 382/131 |
| 2004/0136490 | A1 | 7/2004 | Edic et al. | 378/4 |
| 2008/0091102 | A1 * | 4/2008 | Maeda et al. | 600/436 |
| 2008/0166063 | A1 * | 7/2008 | Zeng | 382/260 |
| 2010/0278412 | A1 * | 11/2010 | Song et al. | 382/131 |
| 2012/0263360 | A1 * | 10/2012 | Zhu et al. | 382/131 |
| 2013/0094739 | A1 * | 4/2013 | Okabe | 382/131 |

OTHER PUBLICATIONS

Flohr, T. G., et al.; First performance evaluation of a dual-source CT (DSCT) system; 2006; Eur. Radiol.; 16:256-268.

Massoumzadeh, P., et al.; Validation of CT dose-reduction simulation; 2009; Med. Phys.; 36(1)174-189.

Roessl, E., et al.; K-edge imaging in x-ray computed tomography using multi-bin photon counting detectors; 2007; Phys. Med. Biol.; 52:4679-4696.

Schlomka, J. P., et al.; Experimental feasibility of multi-energy photon-counting K-edge imaging in pre-clinical computed tomography; 2008; Phys. Med. Biol.; 53:4031-4047.

Stenner, P., et al.; Empirical dual energy calibration (EDEC) for cone-beam computed tomography; 2007; Med. Phys.; 34(9)3630-3641.

Wang, A. S.; Synthetic CT: Simulating low dose single and dual energy protocols from a dual energy scan; 2011; Med. Phys.; 38(10)5551-5555.

* cited by examiner

IMAGING APPARATUS

FIELD OF THE INVENTION

The invention relates to an imaging apparatus, an imaging method and an imaging computer program for imaging an object. The invention relates further to a weighted base function generation apparatus, a weighted base function generation method and a corresponding computer program for generating weighted base functions, which are usable by the imaging apparatus for imaging an object.

BACKGROUND OF THE INVENTION

The article "Empirical dual energy calibration (EDEC) for cone-beam computed tomography" by Philip Stenner et al., Medical Physics, Vol. 34, No. 9, p. 3630-3641 (September 2007) discloses a dual-energy computed tomography system, which generates energy projection data values corresponding to rays after having traversed an object to be imaged, wherein for each ray energy projection data values for two different energies are generated. A decomposition function, which depends on the generated energy projection data values, is used for decomposing the generated energy projection data values into base material projection data values such that for each ray two base material projection data values are determined, which correspond to two different base materials of the object to be imaged. The decomposed base material projection data values are then used for reconstructing a first base material image, which corresponds to a first base material of the object, and a second base material image, which corresponds to a second base material of the object. The decomposition function is a polynomial function, wherein the polynomial's coefficients are determined using a least squares fit based on thresholded images of a calibration phantom.

The decomposition of the initially generated energy projection data values into the base material projection data values can produce artifacts in the determined base material projection data values and, thus, in the finally reconstructed base material images. The quality of the finally reconstructed base material images can therefore be reduced.

SUMMARY OF THE INVENTION

It is an object of the present invention to provide an imaging apparatus, an imaging method and an imaging computer program for imaging an object, wherein the quality of a reconstructed image can be improved. It is a further object of the present invention to provide a weighted base function generation apparatus, a weighted base function generation method and a corresponding computer program for generating weighted base functions, which are usable by the imaging apparatus for imaging an object.

In a first aspect of the present invention an imaging apparatus for imaging an object is presented, wherein the imaging apparatus comprises:

a projection data providing unit for providing energy projection data values, the energy projection data values being energy-dependent and corresponding to rays after having traversed the object, a reconstruction unit for reconstructing an image of the object based on the provided energy projection data values, wherein the reconstruction unit is adapted to:

determine component projection data values, which correspond to the rays after having traversed the object and which correspond to a component of the object, by combining weighted base functions, which depend on the provided energy projection data values, wherein a component projection data value, which corresponds to a ray, is modeled as a combination of weighted base functions, which depend on energy projection data values of the same ray and on the orientation of the same ray, reconstruct an image of the object based on the determined component projection data values.

Since the weighted base functions depend on the orientation of the respective ray, the determination of the component projection data values depending on the provided energy projection data values can consider a possible dependency of the respective decomposition on the orientation of the ray, thereby allowing the imaging apparatus to improve the quality of decomposing the provided energy projection data values into the component projection data values and thus of a finally reconstructed image of the object, which is reconstructed based on the component projection data values.

The projection data providing unit can be a storing unit, in which the energy projection data values are stored already and from which the energy projection data values can be retrieved for providing the same. The projection data providing unit can also be a receiving unit for receiving the energy projection data values from, for example, an energy projection data values acquisition unit and for providing the received energy projection data values. Moreover, the projection data providing unit can also be an acquisition unit for acquiring the energy projection data values like a computed tomography acquisition unit or a nuclear acquisition unit. Preferentially, the projection data providing unit is adapted to provide computed tomography projection data values for different energies as the energy projection data values.

A component of the object, to which the component projection data values can correspond, is, for example, a certain material, in particular, a certain base material, of the object and/or a certain physical effect influencing the rays while traversing the object. The physical effect is, for instance, the photoelectric effect or the Compton effect. The reconstruction unit can be adapted to determine only a single set of component projection data values, which correspond to a certain component of the object, or to determine several sets of component projection data values, which correspond to different components of the object, for example, which correspond to different materials of the object and/or to different physical effects. The reconstruction unit can be adapted to reconstruct an image of the object based on a single set of determined component projection data values or depending on several sets of determined component projection data values. The reconstruction unit can also be adapted to reconstruct several images of the object, wherein each of these images is based on a corresponding single set of determined component projection data values. For example, one or several images can be reconstructed, wherein each image shows a single base material or a single physical effect.

The weighted base functions are preferentially predefined by calibration measurements.

It is preferred that the projection data providing unit is adapted to provide energy projection data values which correspond to rays, which have been emitted by a radiation source and which have traversed the object, wherein the orientation of the rays is defined by at least one of a fan angle, a cone angle and a position of the radiation source. It is further preferred that the weighted base functions are symmetric in at least one of the fan angle and the cone angle. For example, if the orientation is at least defined by a fan angle and/or a cone angle, the weight can depend on the absolute value or the square of the fan angle and/or cone angle. If the weighted base functions depend on the fan-angle, a fan-angle dependent energy spectrum of the radiation, which traverses the object to be imaged, can be considered. A fan-angle dependent spectrum can be caused, for instance, by a beam shaper like a bowtie filter, which may be placed between a radiation source emitting the radiation that traverses the object and the object. If the weighted base functions depend on the cone angle of the respective ray, a cone-angle dependent spectrum can be considered, which can lead to a reduction of Heel effect artifacts in the finally reconstructed image.

The provided energy projected data values have preferentially been acquired, while a radiation source emitting the corresponding rays and the object are moved relative to each other such that rays corresponding to different positions of the radiation source are provided. If the weighted base functions depend on this position of the radiation source, the quality of the decomposition of the energy projection data values into the component projection data values and thus the quality of the finally reconstructed image can be further improved, in particular, if a dynamic bowtie filter is present between the object and the radiation source and if the bowtie filter is dynamically modified depending on the position of the radiation source.

It is preferred that the reconstruction unit is adapted to model a component projection data value as a summation of the weighted base functions. It is further preferred that a base function depends on a product of intermediate base functions, wherein a first intermediate base function depends on the energy projection data values and a second intermediate base function depends on the orientation of the respective ray. The first intermediate base functions can be monomials of the energy projection data values. This allows decomposing the energy projection data values into component projection data values with high quality in a relatively simple way.

It is further preferred that the reconstruction unit is adapted to use different sets of weighted base functions for different kinds of component projection data values. Thus, if, for example, the component projection data values should relate to different base materials of the object, a first set of weighted base functions can be used, and if, for example, the component projection data values should relate to different physical effects, which cause the attenuation of the radiation while traversing the object, a corresponding second set of weighted base functions can be used. Preferentially, the base functions of different sets of weighted base functions are the same, but the weights, with which the base functions are weighted, are different from set to set.

In an embodiment, the imaging apparatus further comprises a calibration image providing unit for providing a component calibration image of a calibration object, wherein the component calibration image corresponds to a component of the calibration object, wherein the projection data providing unit is adapted to provide calibration energy projection data values, the calibration energy projection data values being energy-dependent and corresponding to rays after having traversed the calibration object, wherein the imaging apparatus further comprises a base function providing unit for providing base functions, which depend on energy projection data values corresponding to rays after having traversed the calibration object and which depend on the orientation of the rays, for modeling a component projection data value as a combination of weighted base functions, wherein the reconstruction unit is adapted to provide the weighted base functions by determining weights for weighting the provided base functions by fitting an image of the calibration object, which is reconstructed based on calibration component projection data values, to the provided calibration image, wherein a calibration component projection data value, which corresponds to a ray, is determined as a combination of the weighted provided base functions which depend on calibration energy projection data values of the same ray. This allows providing the weighted base functions just by determining the weights using calibration measurements.

The calibration image providing unit can be adapted to provide several component calibration images of the calibration object, wherein the several component calibration images correspond to several components of the calibration object. For example, a first component calibration image can correspond to a first base material and a second component calibration image can correspond to a second base material, or a first component calibration image can correspond to the photo-electric effect and a second component calibration image can correspond to the Compton effect. Correspondingly, the reconstruction unit can be adapted to provide the weighted base functions by determining several sets of weights for weighting the provided base functions, wherein each of the determined sets of weights corresponds to a certain component of the calibration object. For determining a certain set of weights, the reconstruction unit can fit an image of the calibration object, which is reconstructed based on calibration component projection data values, which correspond to the component of the certain set of weights, to a corresponding provided component calibration image, wherein a calibration component projection data value, which corresponds to a ray, is determined as a combination of the weighted provided base functions, which have been weighted with the certain set of weights and which depend on a calibration energy projection data value of the respective same ray.

In a further aspect of the present invention a weighted base function generation apparatus is presented for generating weighted base functions, which are usable by the imaging apparatus as defined in claim 1 for imaging an object, wherein the weighted base function generation apparatus comprises:
 a calibration image providing unit for providing a component calibration image of a calibration object, which corresponds to a component of the calibration object,
 a projection data providing unit for providing calibration energy projection data values, the calibration energy projection data values being energy-dependent and corresponding to rays after having traversed the calibration object,
 a base function providing unit for providing base functions, which depend on energy projection data values corresponding to rays after having traversed the calibration object and which depend on the orientation of the rays, for modeling a component projection data value as a combination of weighted base functions,
 a reconstruction unit for determining the weighted base functions by determining weights for weighting the provided base functions by fitting an image of the calibration object, which is reconstructed based on calibration component projection data values, to the provided calibration image, wherein a calibration component projection data value, which corresponds to a ray, is determined as a combination of the weighted provided base functions which depend on the provided calibration energy projection data values of the same ray.

Also the weighted base function generation apparatus can be adapted to determine different sets of weights for different components, for example, for different base materials and/or for different physical effects.

In a further aspect of the present invention an imaging method for imaging an object is presented, wherein the imaging method comprises:

provide energy projection data values, the energy projection data values being energy-dependent and corresponding to rays after having traversed the object, by a projection data providing unit, reconstructing an image of the object based on the provided energy projection data values by a reconstruction unit, wherein the reconstruction unit:

determines component projection data values, which correspond to the rays after having traversed the object and which correspond to a component of the object, by combining weighted base functions, which depend on the provided energy projection data values, wherein a component projection data value, which corresponds to a ray, is modeled as a combination of weighted base functions, which depend on energy projection data values of the same ray and on the orientation of the same ray, reconstructs an image of the object based on the determined component projection data values.

In a further aspect of the present invention a weighted base function generation method is presented for generating weighted base functions, which are usable by the imaging method as defined in claim 11 for imaging an object, wherein the weighted base function generation method comprises:

providing a component calibration image of a calibration object, which corresponds to a component of the calibration object, by a calibration image providing unit, providing calibration energy projection data values by a projection data providing unit, the calibration energy projection data values being energy-dependent and corresponding to rays after having traversed the calibration object, providing base functions, which depend on energy projection data values corresponding to rays after having traversed an object and which depend on the orientation of the rays, for modeling a component projection data value as a combination of weighted base functions by a base function providing unit, determining the weighted base functions by determining weights for weighting the provided base functions by fitting an image of the calibration object, which is reconstructed based on calibration component projection data values, to the provided component calibration image by a reconstruction unit, wherein a calibration component projection data value, which corresponds to a ray, is determined as a combination of the weighted provided base functions which depend on the provided calibration energy projection data values of the same ray.

In a further aspect of the present invention an imaging computer program for imaging an object is presented, wherein the imaging computer program comprises program code means for causing an imaging apparatus as defined in claim 1 to carry out the steps of the imaging method as defined in claim 11, when the imaging computer program is run on a computer controlling the imaging apparatus.

In a further aspect of the present invention a computer program for generating weighted base functions is presented, wherein the computer program comprises program code means for causing a weighted base function generation apparatus as defined in claim 12 to carry out the steps of the weighted base function generation method as defined in claim 12, when the computer program is run on a computer controlling the weighted base function generation method.

It shall be understood that the imaging apparatus of claim 1, the weighted base function generation apparatus of claim 10, the imaging method of claim 11, the weighted base function generation method of claim 12, the imaging computer program of claim 13 and the computer program of claim 14 have similar and/or identical preferred embodiments, in particular, as defined in the dependent claims.

It shall be understood that a preferred embodiment of the invention can also be any combination of the dependent claims with the respective independent claim.

BRIEF DESCRIPTION OF THE DRAWINGS

These and other aspects of the invention will be apparent from and elucidated with reference to the embodiments described hereinafter.

In the drawings.

DETAILED DESCRIPTION OF EMBODIMENTS

Figure 1:
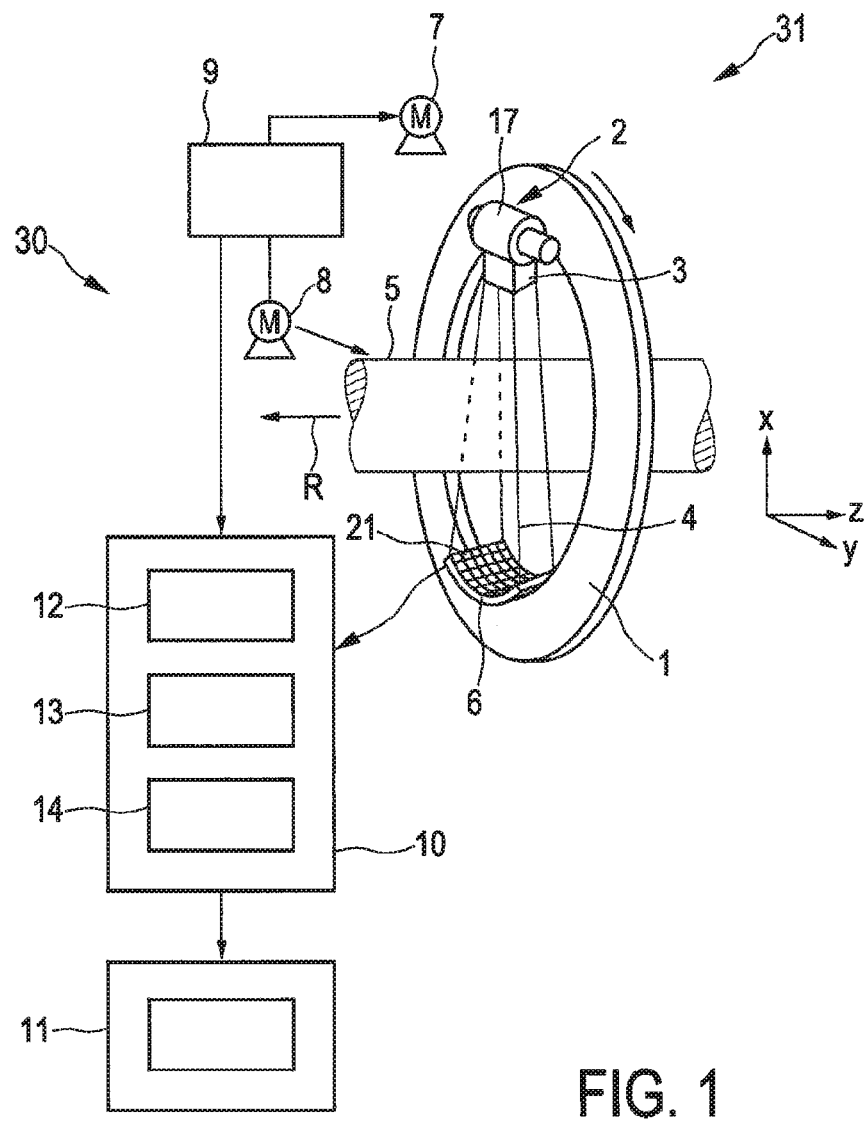
FIG. 1 shows schematically and exemplarily an embodiment of an imaging apparatus for imaging an object.

FIG. 1 shows schematically and exemplarily an imaging apparatus for imaging an object. In this embodiment, the imaging apparatus 31 is a computed tomography apparatus for imaging an object within an examination zone 5. The computed tomography apparatus 31 includes a gantry 1 which is capable of rotation about a rotational axis R which extends parallel to the z direction. A radiation source 2 generates a conical radiation beam 4 for traversing the examination zone 5. The radiation source 2 comprises an x-ray tube 17 and a collimator 3 which forms the conical radiation beam 4 from the radiation generated by the x-ray tube 12. The radiation 4 traverses an object (not shown) such as a patient, which is located within the examination zone 5 being, in this embodiment, cylindrical. After having traversed the object the radiation beam 4 is incident on a detector 6 comprising a two-dimensional detection surface 21. The detector 6 is mounted on the gantry 1.

The computed tomography apparatus 31 comprises two motors 7, 8. The gantry 1 is driven at a preferably constant but adjustable angular speed by the motor 7. The motor 8 is provided for displacing the object, for instance, a patient, who is arranged on a patient table in the examination zone 5, parallel to the direction of the rotational axis R or the z axis. The motors 7, 8 are controlled by a control unit 9 such that the radiation source 2 and the object within the examination zone 5 are moved relative to each other along a helical trajectory. However, the motors 7, 8 can also be controlled such that the radiation source 2 and the object within the examination zone 5 are moved relative to each other along another trajectory. For instance, the motor 7 can drive the gantry 1 such that the radiation source 2 rotates around the object within the examination zone 5, while the motor 8 does not move the object parallel to the direction of the rotational axis R or the z axis. In this case, the radiation source 2 and the object within the examination zone 5 are moved relative to each other along a circular trajectory. During the relative movement of the radiation source 2 and the object within the examination zone 5 the detector 6 generates energy projection data values being indicative of the radiation beam 4 after having traversed the object.

The motors 7, 8, the radiation source 2, the detector 6, the gantry 1 and the control unit 9 form a computed tomography acquisition unit 30 being the projection data providing unit for providing energy projection data values, which are energy-dependent and which correspond to rays of the radiation beam 4 after having traversed the object.

The provided energy projection data values comprise for each ray two energy projection data values, which correspond to two different energies. In this embodiment, the two different energies are provided by the detector 6, which is formed as a double-decker detection system as disclosed in, for example, the article "Material separation with dual-layer CT" by R. Carmi et al., Nuclear Science Symposium Conference Record, IEEE, pages 1876 to 1878, 2005, which is herewith incorporated by reference. However, in other embodiments the two energies can also be provided by using another projection data acquisition unit, in particular, by using another computed tomography projection data acquisition unit. For instance, a computed tomography acquisition unit having two different x-ray tubes emitting radiation with two different energies can be provided as disclosed in, for example, the article "First performance evaluation of a dual-source CT (DSCT) system" by T. G. Mohr et al., European Radiology, volume 16, pages 256 to 268 (2006), which is herewith incorporated by reference. Or the detector can be a photon-counting detector as disclosed in, for example, the articles "K-edge imaging in x-ray computed tomography using multi-bin photon counting detectors", E. Roessl et al., Physics in Medicine and Biology, volume 52, pages 4679-4696 (2007) and "Experimental feasibility of multi-energy photon-counting K-edge imaging in pre-clinical computed tomography", J. P. Schlomka et al., Physics in Medicine and Biology, volume 53, pages 4031 to 4047 (2008), which are herewith incorporated by reference.

The provided energy projection data values can also comprise more than two energy projection data values, which correspond to more than two different energies, for each ray. For example, two dual-energy techniques can be combined for providing energy projection data values comprising for each ray four energy projection data values, which correspond to four different energies, i.e., in an embodiment, the energy projection data values can be provided by a quad-energy CT system.

Each provided energy projection data value corresponds to a certain ray and, thus, to a certain orientation of the ray. In this embodiment, the orientation of a ray is defined by the position of the radiation source, the fan angle and the cone angle. The fan angle is defined as the angle between a projection of the respective ray in a plane being perpendicular to the rotational axis R and containing the respective radiation source position and a line, which is located in the same plane and which connects the respective radiation source position with the rotational axis R. The cone angle can be defined in a plane containing the rotational axis R and the respective radiation source position, wherein the cone angle is the angle between a projection of the respective ray on this plane and a line, which is located within this plane and centrally within the radiation beam 4.

The computed tomography apparatus 31 further comprises a reconstruction 12 for reconstructing an image of the object within the examination zone 5 based on the provided energy projection data values. In particular, the reconstruction unit 12 is adapted to determine component projection data values, which correspond to the rays after having traversed the object, by combining weighted base functions, which depend on the provided energy projection data values, wherein a component projection data value, which corresponds to a ray, is modeled as a combination of weighted base functions which depend on energy projection data values of the same way, and wherein the weighted base functions depend on the orientation of the ray. The reconstruction unit 12 reconstructs then an image of the object within the examination zone 5 based on the determined component projection data values.

The orientation of the respective ray is defined by the fan angle, the cone angle and the respective position of the radiation source. The weighted base functions can depend on one, two or all of the fan angle, the cone angle and the position of the radiation source.

In this embodiment the weighted base functions depend only on the fan angle. However, in other embodiments, alternatively or in addition, the weighted base functions can depend on the cone angle and/or the position of the radiation source. The reconstruction unit 12 can be adapted to determine component projection data values $A_i^q$ for the i-th ray and for the q-th component in accordance with following equation:

$$A_i^q = \sum_{m=1}^{M} \sum_{l=1}^{L} c_m^{lq} B_m^l(l_i^1, l_i^2, \varphi_i^2), \quad (1)$$

wherein $c_m^{lq}$ denotes weights for weighting the base functions and $B_m^l(l_i^1, l_i^2, \phi_i^2)$ denotes the base functions, which depend on energy projection data values $l_i^1, l_i^2$ for two different energies indicated by the indices 1 and 2 and the same i-th ray and which depend on the square of the fan angle $\phi_i$ of the same i-th ray. In this embodiment, the base functions are therefore symmetric in the fan angle. The base functions can be defined by the following equation:

$$B_m^l(l_i^1, l_i^2, \phi_i^2) = f_l(\phi_i^2) b_m(l_i^1, l_i^2). \quad (2)$$

Thus, a base function is preferentially a product of a first intermediate base function $b_m^l(l_i^1, l_i^2)$, which depends on the energy projection data values, and a second intermediate base function $f_l(\phi_i^2)$, which depends on the square of the fan angle. The first intermediate base functions are preferentially monomials of the energy projection data values, which can be defined, for example, as follows: $b_1(l_i^1, l_i^2) = l_i^1$, $b_2(l_i^1, l_i^2) = l_i^2$, $b_3(l_i^1, l_i^2) = (l_i^1)^2$, $b_4(l_i^1, l_i^2) = (l_i^2)^2$, $b_5(l_i^1, l_i^2) = l_i^1 l_i^2$.

In this example, five first intermediate base functions are defined, i.e. M is 5. However, in other embodiments, M can also have another value. In general, the variables M and L are predefined such that the below described calibration procedure is optimized. The second intermediate base functions $f_l(\phi_i^2)$ are preferentially even powers of the fan angle. For example, following functions can be provided as the second intermediate base functions: $f_1(\phi_i^2) = \phi_i^2$, $f_2(\phi_i^2) = \phi_i^4$, $f_3(\phi_i^2) = \phi_i^6$. In this example, three second intermediate base functions are defined, i.e. L is 3. However, in other embodiments, L can also have another value.

The reconstruction unit 5 is preferentially adapted to reconstruct an image of the object based on the determined component projection data values by using, for example, a filtered back projection algorithm, a Radon inversion algorithm, or another reconstruction algorithm.

The reconstruction unit 12 can be adapted to use different sets of weighted base functions for different kinds of component projection data values. For example, if the provided energy projection data values should be decomposed into base material projection data values, a first corresponding set of weighted base functions can be provided, and, if the energy projection data values should be decomposed into, for example, photo-electric effect projection data values and Compton effect projection data values, a corresponding second set of weighted base functions can be provided. Different sets of weighted base functions can be determined by calibration as will be described in the following.

A calibration object having known component distributions is arranged within the examination zone 5, wherein corresponding component calibration images, which show the known component distributions, are provided by a calibration image providing unit 13. For example, a first component calibration image can be provided, which shows a first base material distribution or a first physical effect distribution, and a second component calibration image can be provided, which shows a second base material distribution or a second physical effect distribution. Then, a calibration scan is performed for providing calibration energy projection data values, wherein the calibration energy projection data values are energy-dependent and correspond to rays after having traversed the calibration object. In particular, the calibration energy projection data values as well as the above mentioned energy projection data values, which are generated in an actual scan, depend on the intensities of the rays after having traversed the calibration object.

The imaging apparatus 1 further comprises a base function providing unit 14 for providing predefined base functions, which depend on energy projection data values corresponding to rays after having traversed the calibration object and which depend on the orientation of the rays, for modeling a component projection data value as a combination of weighted base functions. In this embodiment, the base function providing unit 14 provides the base functions defined in equation (2).

The reconstruction unit 12 can be adapted to provide the weighted base functions by determining weights $c_m^{lq}$ for weighting the provided base functions $B_m^l(l_i^1, l_i^2, \phi_i^2)$ by fitting an image of the calibration object, which is reconstructed based on calibration component projection data values, to the respective provided component calibration image, wherein a calibration component projection data value, which corresponds to a ray, is determined as a combination of the weighted provided base functions which depend on calibration energy projection data values of the same ray. Thus, the weights $c_m^{lq}$ can be modified such that a similarity measure indicating the degree of similarity between the reconstructed image of the calibration object and the respective provided component calibration image is optimized. The similarity measure is, for example, the sum of squared differences of image values of corresponding pixels or voxels in the two images. The reconstruction of the image of the calibration object can be performed in accordance with following equation:

$$a_j^{cq} = \Re^{-1}(A_i^{cq}) = \sum_{m=1}^{M}\sum_{l=1}^{L} c_m^{lq} \Re^{-1}(B_m^l(l_i^{1,c}, l_i^{2,c}, \varphi_i^2)), \quad (3)$$

wherein $a_j^{cq}$ denotes the image values of the reconstructed image of the calibration object, which corresponds to the q-th component, indexed by the index j, $\Re^{-1}$ denotes a linear reconstruction operation like an inverse Radon transform operation, $A_i^{cq}$ denotes calibration component projection data values for the i-th ray and the q-th component, $A_i^{lq}$ denotes the fitted weights, $B_m^l(l_i^{1,c}, l_i^{2,c}, \phi_i^2)$ denotes the provided predefined base functions and $l_i^{1,c}$, $l_i^{2,c}$ denote the provided calibration energy projection data values for two different energies and for the i-th ray.

The reconstruction unit 12 can be adapted to firstly perform the reconstruction operations $\Re^{-1}(B_m^l(l_i^{1,c}, l_i^{2,c}, \phi_i^2))$, in order to produce several corresponding intermediate images, wherein then the weights $c_m^{lq}$ are modified, i.e. determined, such that a difference measure between $a_j^{cq}$ and the corresponding provided component calibration image is minimized. The difference measure is, for example, based on squared differences between corresponding image values in the reconstructed image $a_j^{cq}$ and in the corresponding component calibration image.

Thus, in the calibration procedure the weights $c_m^{lq}$ can be determined in accordance with equation (3), wherein, after the calibration procedure has been completed, the provided predefined base functions together with the calibrated weights can be used as weighted base functions for determining the component projection data values in accordance with equation (1) in an actual scan of an unknown object.

The reconstructed images are provided to a display unit 11 for displaying the reconstructed images.

Although in the embodiment described above with reference to FIG. 1 the computed tomography apparatus 31 is capable of determining the weighted base functions by performing the above mentioned calibration procedure and of reconstructing an image of an unknown object based on acquired energy projection data values and the determined weighted base functions, the computed tomography apparatus can also be adapted to just use already determined weighted base functions, without having the capability of determining the weighted base functions by performing the above mentioned calibration procedure. In this case, the weighted base functions are determined by using a weighted base function generation apparatus, which is capable of performing the above described calibration procedure, wherein the generated weighted base functions are provided to an imaging apparatus, which may not have the capability of performing the calibration procedure.

Figure 2:
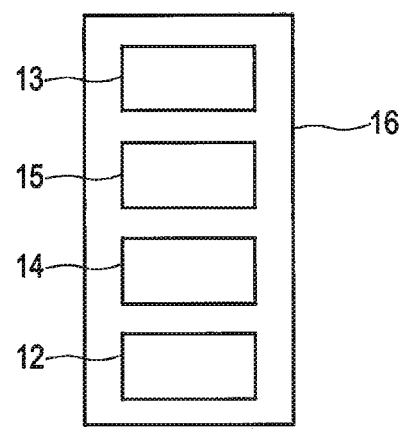
FIG. 2 shows schematically and exemplarily an embodiment of a weighted base function generation apparatus for generating weighted base functions.

FIG. 2 shows schematically and exemplarily an embodiment of a weighted base function generation apparatus for generating weighted base functions, which are usable by an imaging apparatus as described above with reference to FIG. 1.

The weighted base function generation apparatus 16 comprises a calibration image providing unit 13 for providing a component calibration image of a calibration object showing a known component distribution of the calibration object. The weighted base function generation apparatus 16 further comprises a projection data providing unit 15 for providing calibration energy projection data values. The calibration energy projection data values are energy-dependent and correspond to rays after having traversed the calibration object. In this embodiment, the projection data providing unit 15 is a storing unit, in which the calibration energy projection data values are stored already. In another embodiment, the projection data providing unit can also be a receiving unit for receiving calibration energy projection data values and for providing the received energy projection data values. The projection data providing unit can also be a projection data acquisition unit, in particular, a computed tomography projection data acquisition unit, for acquiring calibration energy projection data values and for providing the acquired calibration energy projection data values.

The weighted base function generation apparatus 16 further comprises a base function providing unit 14 for providing base functions, which depend on energy projection data values corresponding to rays after having traversed the calibration object and which depend on the orientation of the rays, for modeling a component projection data value as a combination of weighted base functions. Moreover, the weighted base function generation apparatus 16 comprises a reconstruction unit 12 for determining the weighted base functions by determining weights for weighting the provided base functions by fitting an image of the calibration object, which is reconstructed based on calibration component projection data values, to the provided component calibration image, wherein a calibration component projection data value, which corresponds to a ray, is determined as a combination of the weighted provided base functions, which depend on the provided calibration energy projection data values of the same ray.

Also the weighted base function generation apparatus can be adapted to determine several sets of weights for different components of the object by using different corresponding component calibration images.

Figure 3:
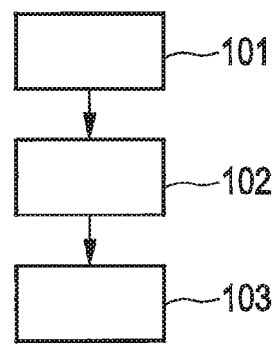
FIG. 3 shows a flowchart exemplarily illustrating an imaging method for imaging an object.

In the following an embodiment of an imaging method for imaging an object will exemplarily be described with reference to a flowchart shown in FIG. 3.

In step 101, energy projection values are provided by the projection data providing unit 30. The energy projection data values are energy-dependent and correspond to rays after having traversed the object within the examination zone 5. In particular, the radiation source 2 is moved relative to the object for acquiring energy projection data values in different angular directions. In step 102, the reconstruction unit 12 determines component projection data values, which correspond to the rays after having traversed the object within the examination zone 5, by combining weighted base functions, which depend on the provided energy projection data values, wherein a component projection data value, which corresponds to a ray, is modeled as a combination of weighted base functions which depend on energy projection data values of the same ray. The weighted base functions depend on the orientation of the respective ray. In this embodiment, the weighted base functions have already been determined by calibration measurements and the weighted base functions depend on the fan angle. In step 103, an image of the object is reconstructed based on the determined component projection data values.

Figure 4:
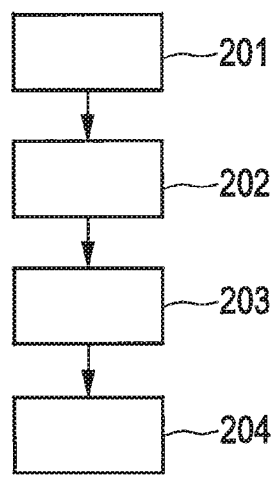
FIG. 4 shows a flowchart exemplarily illustrating an embodiment of a weighted base function generation method for generating weighted base functions.

In the following an embodiment of a weighted base function generation method for generating weighted base functions will exemplarily be described with reference to a flowchart shown in FIG. 4.

In step 201, a component calibration image of a calibration object, which has a known component distribution, is provided by the calibration image providing unit 13. In step 202, calibration energy projection data values are provided by the projection data providing unit 15. The calibration energy projection data values are energy-dependent and correspond to rays after having traversed the calibration object. In step 203, base functions are provided by the base function providing unit 14. The base functions depend on energy projection data values corresponding to rays after having traversed an object and on the orientation of the rays. The base functions are adapted to model a component protection data value as a combination of weighted base functions. In step 204, weighted base functions are determined by determining weights for weighting the provided base functions by fitting an image of the calibration object, which is reconstructed based on calibration component projection data values, to the provided component calibration image by the reconstruction unit 12. A calibration component projection data value, which corresponds to a ray, is determined as a combination of the weighted provided base functions which depend on the provided calibration energy projection data values of the same ray.

The imaging apparatus and the imaging method are preferentially adapted to perform a dual-energy component decomposition without the need for prior spectral knowledge such as the energy spectrum of the radiation, the sensitivity functions of the detector and/or specific properties of radiation filters for filtering the radiation. The imaging apparatus and imaging method are preferentially based on a pre-calibration in the form of a spectral scan of a dedicated calibration phantom, i.e. the calibration object. The resulting calibration data are used for decomposing energy projection data values into component projection data values.

The above mentioned article by Stenner et al. assumes that the spectral inversion of the measurements of the intensity of the radiation is the same for all detector pixels of an x-ray detector. This assumption constitutes a serious drawback in the case of commercial computed tomography scanners where beam shapers are applied to equalize the x-ray flux on the detector in the presence of a patient. Side-effects of the flux homogeneity are then different levels of beam hardening along the fan angle.

The imaging apparatus and imaging method in accordance with the invention does preferentially not assume a homogeneous spectral inversion of measurements, i.e. of energy projection data values, for different detector pixels of the detector. In particular, the imaging apparatus and imaging method include the case of fan-angle dependent decomposition polynomials as described above.

While the invention has been illustrated and described in detail in the drawings and foregoing description, such illustration and description are to be considered illustrative or exemplary and not restrictive; the invention is not limited to the disclosed embodiments.

In particular, although in the above described embodiments the imaging apparatus is a computed tomography apparatus, in other embodiments the imaging apparatus can also be another imaging modality which provides energy projection data values.

Although in the above described embodiments for a same ray two energy projection data values are provided, which correspond to two different energies, in other embodiments also more than two energy projection data values, which correspond to more than two energies, can be provided for a same ray.

Although in the above described embodiments the weighted base functions depend on the fan angle only, the weighted base function can also depend on another parameter describing the orientation of the ray. For example, the weighted base functions can depend on the fan angle and at least one of the cone angle and the radiation source position. If the weighted base functions also depend on the cone angle and the radiation source position, the reconstruction can be adapted to determine component projection values in accordance with following equation:

$$A_i^q = \sum_{m=1}^{M} \sum_{l=1}^{L} \sum_{k=1}^{K} \sum_{n=1}^{N} c_{mn}^{lqk} B_{mn}^{lk}(l_i^1, l_i^2, \varphi_i, \vartheta_j, p_i) \text{ with} \quad (4)$$

$$B_{mn}^{lk}(l_i^1, l_i^2, \varphi_i, \vartheta_j, p_i) = g_n(p_i)h_k(\vartheta_j)d_l(\varphi_i)b_m(l_i^1, l_i^2). \quad (5)$$

The reconstruction unit can be adapted to reconstruct an image of the object based on the component projection data values as defined by equation (4). The calibration procedure for determining the weights $C_{mn}^{lqk}$ can be performed in accordance with following equation:

$$a_j^{cq} = \Re^{-1}(A_i^{cq}) = \sum_{m=1}^{M}\sum_{l=1}^{L}\sum_{k=1}^{K}\sum_{n=1}^{N} c_{mn}^{lqk} \Re^{-1}(B_{mn}^{lk}(l_i^{1,c}, l_i^{2,c}, \varphi_i^c, \vartheta_i^c, p_i^c)). \quad (6)$$

Equation (4) corresponds to equation (1), equation (5) corresponds to equation (2) and equation (6) corresponds to equation (3). The variables M, L, K and N are preferentially chosen such that the above described calibration procedure is optimized. In the equations, $B_{mn}^{lk}(l_i^1, l_i^2, \phi_i, \vartheta_i, p_i)$ denotes the base functions, which depend on the energy projection data values $l_i^1, l_i^2$, the fan angle $\phi_i$, the cone angle $\vartheta_i$ and an index $p_i$ indicating the position of the radiation source for the i-th ray. Moreover, $g_n(p_i)$ denotes an intermediate base function depending on the position of the radiation source, $h_k(\vartheta_i)$ denotes an intermediate base function depending on the cone angle and $d_l(\phi_i)$ denotes an intermediate base function depending on the fan angle.

The imaging apparatus is preferentially a computed tomography apparatus, wherein between the object to be imaged and the radiation source preferentially a beam shaper like a bowtie filter, in particular, a dynamic bowtie filter is arranged. A dynamic bowtie filter is preferentially a bowtie filter, which changes its attenuation of the radiation depending on the position of the radiation source.

Although the variables $l_i^1, l_i^2$, have been described as being energy projection data values, these variables can also indicate other values, which depend on the provided energy projection data values. For example, they can indicate measured line integrals along the respective ray, which can be determined from the corresponding energy projection data value.

The above described intermediate base functions, which depend on the fan angle or the cone angle, can also depend on another variable, which depends on the cone angle or the fan angle. For example, if a beam shaper is provided between the radiation source and the object to be imaged, the length of the respective ray within the beam shaper depends on the cone angle and/or the fan angle. Thus, the corresponding intermediate base functions can also depend on this length, in order to indirectly consider the dependence of the weighted base functions on the fan angle and/or the cone angle.

Calculations like the determination of component projection data values and the reconstruction of an image of the object performed by one or several units or devices can be performed by any other number of units or devices. For example, steps 102 and 103 can be performed by a single unit or by any other number of different units. The calculations and/or the control of the imaging apparatus in accordance with the imaging method and/or the control of the weighted base function generation apparatus in accordance with the weighted base function generation method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to an imaging apparatus for imaging an object. A reconstruction unit determines component projection data values, which correspond to, for example, a base material of the object, and reconstructs an image of the object based on the determined component projection data values. A component projection data value, which corresponds to a ray, is determined as a combination of weighted base functions, which depend on energy projection data values of the same ray and the orientation of the same ray. This allows considering a possible dependency of the corresponding decomposition on the orientation of the ray, thereby allowing the imaging apparatus to improve the quality of decomposing the provided energy projection data values into the component projection data values and thus of a finally reconstructed image of the object, which is reconstructed based on the component projection data values.

The invention claimed is:

1. An imaging apparatus for imaging an object, the imaging apparatus comprising:
    a projection data providing unit for providing energy projection data values, the energy projection data values being energy-dependent and corresponding to rays, which have been emitted by a radiation source and which have traversed the object and a beam shaper placed between the radiation source and the object,
    a reconstruction unit for reconstructing an image of the object based on the provided energy projection data values, wherein the reconstruction unit is adapted to:
    determine component projection data values, corresponding to the rays after having traversed the object and to a component of the object, by combining weighted base functions based on the provided energy projection data values and a component projection data value corresponding to a ray modeled as a combination of weighted base functions, wherein said weighted base function depends on a product of a first intermediate base function and a second intermediate based function, wherein said first intermediate base function depends on the energy projection data values and said second intermediate base function depends on the length of the respective ray within the beam shaper,
    reconstruct an image of the object based on the determined component projection data values.

2. The imaging apparatus as defined in claim 1, wherein the weighted base functions depend on the orientation of the respective ray, wherein the orientation of the rays is defined by at least one of a fan angle, a cone angle and a position of the radiation source.

3. The imaging apparatus as defined in claim 2, wherein the weighted base functions are symmetric in at least one of the fan angle and the cone angle.

4. The imaging apparatus as defined in claim 1, wherein the reconstruction unit is adapted to model a component projection data value as a summation of the weighted base functions.

5. The imaging apparatus as defined in claim 1, wherein the first intermediate base functions are monomials of the energy projection data values.

6. The imaging apparatus as defined in claim 1, wherein the reconstruction unit is adapted to model component projection data values which correspond to at least one of different materials of the object and different physical effects influencing the rays while traversing the object.

7. The imaging apparatus as defined in claim 1, wherein the reconstruction unit is adapted to use different sets of weighted base functions for different kinds of component projection data values.

8. The imaging apparatus as defined in claim 1, wherein
the imaging apparatus further comprises a calibration image providing unit for providing a component calibration image of a calibration object, wherein the component calibration image corresponds to a component of the calibration object,
the projection data providing unit is adapted to provide calibration energy projection data values, the calibration energy projection data values being energy-dependent and corresponding to rays, which have been emitted by a radiation source and which have traversed the calibration object and a beam shaper placed between the radiation source and the calibration object,
the imaging apparatus further comprises a base function providing unit for providing base functions for modeling a component projection data value as a combination of weighted base functions, wherein a base function depends on a product of intermediate base functions, wherein a first intermediate base function depends on the energy projection data values and a second intermediate base function depends on the length of the respective ray within the beam shaper,
the reconstruction unit is adapted to provide the weighted base functions by determining weights for weighting the provided base functions by fitting an image of the calibration object, which is reconstructed based on calibration component projection data values, to the provided component calibration image, wherein a calibration component projection data value, which corresponds to a ray, is determined as a combination of the weighted provided base functions which depend on calibration energy projection data values of the same ray.

9. A weighted base function generation apparatus for generating weighted base functions, which are usable by the imaging apparatus as defined in claim 1 for imaging an object, wherein the weighted base function generation apparatus comprises:
a calibration image providing unit for providing a component calibration image of a calibration object, which corresponds to a component of the calibration object,
a projection data providing unit for providing calibration energy projection data values, the calibration energy projection data values being energy-dependent and corresponding to rays, which have been emitted by a radiation source and which have traversed the calibration object and a beam shaper placed between the radiation source and the calibration object,
a base function providing unit for providing base functions for modeling a component projection data value as a combination of weighted base functions, wherein a base function depends on a product of intermediate base functions, wherein a first intermediate base function depends on energy projection data values corresponding to the respective ray after having traversed the calibration object and a second intermediate base function depends on the length of the respective ray within the beam shaper,
a reconstruction unit for determining the weighted base functions by determining weights for weighting the provided base functions by fitting an image of the calibration object, which is reconstructed based on calibration component projection data values, to the provided component calibration image, wherein a calibration component projection data value, which corresponds to a ray, is determined as a combination of the weighted provided base functions which depend on the provided calibration energy projection data values of the same ray.

10. An imaging method for imaging an object, the imaging method comprising:
providing energy projection data values, the energy projection data values being energy-dependent and corresponding to rays, which have been emitted by a radiation source and which have traversed the object and a beam shaper placed between the radiation source and the object, by a projection data providing unit,
reconstructing an image of the object based on the provided energy projection data values by a reconstruction unit, wherein the reconstruction unit:
determines component projection data values, corresponding to the rays after having traversed the object and to a component of the object, by combining weighted base functions based on the provided energy projection data values and a component projection data value, corresponding to a ray modeled as a combination of weighted base functions, wherein a base function depends on a product of intermediate base functions and a second intermediate based function wherein said first intermediate base function depends on the energy projection data values and said second intermediate base function depends on the length of the respective ray within the beam shaper,
reconstructs an image of the object based on the determined component projection data values.

11. A weighted base function generation method for generating weighted base functions, which are usable by the imaging method as defined in claim 10 for imaging an object, wherein the weighted base function generation method comprises:
providing a component calibration image of a calibration object, which corresponds to a component of the calibration object, by a calibration image providing unit,
providing calibration energy projection data values by a projection data providing unit, the calibration energy projection data values being energy-dependent and corresponding to rays, which have been emitted by a radiation source and which have traversed the calibration object and a beam shaper placed between the radiation source and the calibration object,
providing base functions, for modeling a component projection data value as a combination of weighted base functions by a base function providing unit, wherein a base function depends on a product of intermediate base functions, wherein a first intermediate base function depends on energy projection data values corresponding to a respective ray after having traversed an object and a second intermediate base function depends on the length of the respective ray within the beam shaper,
determining the weighted base functions by determining weights for weighting the provided base functions by fitting an image of the calibration object, which is reconstructed based on calibration component projection data values, to the provided component calibration image by a reconstruction unit, wherein a calibration component projection data value, which corresponds to a ray, is determined as a combination of the weighted provided base functions which depend on the provided calibration energy projection data values of the same ray.

12. A computer program for imaging an object and stored on a non-transitory computer-readable medium, the computer program comprising program code means for causing an imaging apparatus to carry out the steps of the imaging method as defined in claim 10, when the computer program is run on a computer controlling the imaging apparatus.

13. A computer program for generating weighted base functions and stored on a non-transitory computer-readable medium, the computer program comprising program code means for causing a weighted base function generation apparatus to carry out the steps of the weighted base function generation method as defined in claim 11, when the computer program is run on a computer controlling the weighted base function generation method.

* * * * *